(12) United States Patent
Fahmi et al.

(10) Patent No.: US 7,737,132 B2
(45) Date of Patent: Jun. 15, 2010

(54) β-CYCLODEXTRIN DERIVATIVES AS ANTIBACTERIAL AGENTS

(75) Inventors: Noureddine Fahmi, Charlottesville, VA (US); Frank Werner Schmidtmann, Charlottesville, VA (US); Sidney Hecht, Charlottesville, VA (US)

(73) Assignee: Pinnacle Pharmaceuticals, Charlottesville, VA (US)

(*) Notice: Subject to any disclaimer, the term of this patent is extended or adjusted under 35 U.S.C. 154(b) by 572 days.

(21) Appl. No.: 11/342,339

(22) Filed: Jan. 27, 2006

(65) Prior Publication Data
US 2006/0199785 A1    Sep. 7, 2006

Related U.S. Application Data

(60) Provisional application No. 60/647,841, filed on Jan. 28, 2005.

(51) Int. Cl.
*A61K 31/724*    (2006.01)
*C08B 3/18*    (2006.01)

(52) U.S. Cl. .......................................... 514/58; 536/46
(58) Field of Classification Search .................. 514/58; 536/46
See application file for complete search history.

(56) References Cited

U.S. PATENT DOCUMENTS

| | | | |
|---|---|---|---|
| 4,247,535 A | 1/1981 | Lewis et al. | |
| 4,258,180 A | 3/1981 | Lewis et al. | |
| 5,250,520 A | 10/1993 | Kurita et al. | |
| 5,585,216 A | 12/1996 | Baur et al. | |
| 5,599,912 A | 2/1997 | Rodell et al. | |
| 5,728,823 A | 3/1998 | Reuscher et al. | |
| 5,739,121 A | 4/1998 | Wiebe et al. | |
| 5,760,017 A | 6/1998 | Djedaini-Pilard et al. | |
| 5,800,602 A | 9/1998 | Baur et al. | |
| 5,821,349 A | 10/1998 | Djedaini-Pilard et al. | |
| 5,834,446 A | 11/1998 | Dow et al. | |
| 5,959,089 A | 9/1999 | Hanessian et al. | |
| 6,042,723 A | 3/2000 | Duval et al. | |
| 6,180,356 B1 | 1/2001 | London et al. | |
| 6,632,748 B2 | 10/2003 | Yim et al. | |
| 6,716,827 B1 | 4/2004 | Roselli et al. | |
| 6,858,723 B1 | 2/2005 | Auzely-Velty et al. | |
| 7,169,477 B2 | 1/2007 | Lyu et al. | |
| 2005/0059634 A1 | 3/2005 | Venton et al. | |
| 2007/0021380 A1 | 1/2007 | Wiebe et al. | |

FOREIGN PATENT DOCUMENTS

| | | |
|---|---|---|
| DE | 2425663 | 12/1975 |
| DE | 3710569 | 5/1988 |
| DE | 4136325 | 5/1993 |
| DE | 19520967 | 12/1996 |
| DE | 19520989 | 12/1996 |
| EP | 1245628 | 10/2002 |
| ES | 2053399 | 7/1994 |
| FR | 2669535 | 5/1992 |
| FR | 2878853 | 6/2006 |
| GB | 2261740 | 5/1993 |
| JP | 49085015 | 8/1974 |
| JP | 50140476 | 11/1975 |
| JP | 51142088 | 12/1976 |
| JP | 52138580 | * 11/1977 |
| JP | 53049089 | 5/1978 |
| JP | 03075634 | 3/1991 |
| JP | 06065307 | 3/1994 |
| JP | 10060006 | 3/1998 |
| JP | 2005290066 | 10/2005 |
| WO | WO95/17191 | 6/1995 |
| WO | WO97/49735 | 12/1997 |
| WO | WO99/50307 | 10/1999 |
| WO | WO01/40316 | 6/2001 |
| WO | WO01/83564 | 11/2001 |
| WO | WO01/98370 | 12/2001 |
| WO | WO02/077000 | 10/2002 |
| WO | WO2004/014959 | 2/2004 |
| WO | WO2004/085487 | 10/2004 |
| WO | WO2004/087768 | 10/2004 |
| WO | WO2005/042590 | 4/2005 |
| WO | WO2006/027631 | 3/2006 |
| WO | WO2006/075580 | 7/2006 |

OTHER PUBLICATIONS

Croft et al, Tetrahedron 1983, 39(9), 1417-1474.*
Salem et al, Intl. J. Pharm. 2003, 250, 403-414.*
Athanassiou et al, Journal of Pharmacy and Pharmacology, 2003, 55, 291-300.*
Croft et al., "Synthesis of Chemically Modified Cyclodextrins", Tetrahedron, 39(9):1417-1474 (1983).
Castro-Hermida et al., "Treatment With B-Cyclodextrin of Natural Cryptosporidium Parvum Infections in Lambs Under Field Conditions", International Journal for Parasitology, 21:1134-1137 (2001).
Salem et al., "Efficacies of Cyclodextrin-Complexed and Liposome-Encapsulated Clarithromycin Against Mycobacterium Avium Complex Infection in Human Macrophages", International Journal of Pharmaceutics, 250:403-414 (2003).
Remington's Pharmaceutical Sciences, 18th Edition, ed. A. Gennaro, Mack Publishing Co., Easton, PA (1990).
Karginov et al., "Search for cyclodextrin-based inhibitors of anthrax toxins: synthesis, structural features, and relative activities"; Antimicrobial Agents and Chemotherapy (2006), 50(11),3740-3753.
Wang et al., "Per-6-substituted-per-6-deoxy-β-cyclodextrins Inhibit the Formation of β-Amyloid Peptide Derived Soluble Oligomers"; Journal of Medicinal Chemistry (2004), 47(13),3329-3333.

(Continued)

*Primary Examiner*—Shaojia Anna Jiang
*Assistant Examiner*—Ganapathy Krishnan
(74) *Attorney, Agent, or Firm*—Sterne, Kessler, Goldstein & Fox P.L.L.C.

(57) ABSTRACT

The invention provides a new class of antibiotics to which pathogenic bacteria have not been exposed, and thus should not have developed resistance. This new class of antibiotics are derivatives of β-cyclodextrin (β-CD), which is a cyclic molecule comprising seven D-glucose units.

44 Claims, No Drawings

OTHER PUBLICATIONS

Vizitiu et al. "Synthesis of Mono-facially Functionalized Cyclodextrins Bearing Amino Pendent Groups"; Journal of Organic Chemistry (1997), 62(25), 8760-8766.
Dixon et al., "Anthrax", N. Engl. J. Med., 341(11):815-826 (1999).
Brossier et al., "Toxins of *Bacillus anthracis*", Toxicon, 39:1747-1755 (2001).
Petosa et al., "Crystal Structure of the Anthrax Toxin Protective Antigen", Nature, 385:833-838 (1997).
Karginov et al., "Treatment of Anthrax Infection With Combination of Ciproflaxacin and Antibodies to Protective Antigen of *Bacillus anthracis*", FEMS Immun. Med. Microb., 40:71-74 (2004).
Baer et al., "Improved Preparation of Hexakis(6-deoxy)cyclomaltohexaose and Heptakis(6-deoxy)cyclomaltoheptaose", Carbohydr. Res., 228:307-314 (1992).
Iwata et al., "Manufacture of Cyclodextrin Derivatives", Jpn. Kokai Tokkyo Koho, 9pp. (1989).
Minora et al., "Amino Acid Polymers Containing Cyclodextrin in the Main Chain and their Preparation" Jpn. Kokai Tokkyo Koho 5pp., (1994).
Fukuhara et al., "Synthesis and characterization of the first pair of an unlocked and a locked self-inclusion complex from a permethylated alpha-cyclodextrin derivative", Chem. Letters 32(6):536-537, (2003).
Kurita et al., "Cyclodextrin Derivatives", Jpn. Kokai 7pp (1974).
Karginov et al., "β-Cyclodextrin derivatives that inhibit anthrax lethal toxin"; Bioorganic & Medicinal Chemistry, 14(1), 33-40 (2006).
Hoogenboom et al. "Synthesis of star-shaped poly(.vepsiln.-caprolactone) via 'click' chemistry and 'supramolecular click' chemistry"; Chemical Communications (Cambridge, United Kingdom) (38), 4010-4012 (2006).
Casas-Solvas et al. "Synthesis of Nitrogen-Functionalized β-Cycloaltrins", Journal of Organic Chemistry, 69(25), 8942-8945 (2004).
Kraus et al. "A homologous series of persubstituted cyclodextrin amino acids:The quest for tubular self-assembly", European Journal of Organic Chemistry, (19), 4060-4069 (2004).
Sallas et al. "A practical synthesis of amphiphilic cyclodextrins fully substituted with sugar residues on the primary face", Chemical Communications (Cambridge, United Kingdom) (5), 596-597(2004).
Mourtzis et al. "Influence of Host's Substitution on the Orientation of the Guest: Pseudo-rotaxanes of Charged Cyclodextrins with Methyl Orange in Solution"; Supramolecular Chemistry, 16(8), 587-593 (2004).
Heck et al. "Heptakis-6-(5-methylene-thioureido-5'-methyl-2,2'-bipyridyl)-β-cyclodextrin: synthesis and metal complexation study"; Tetrahedron Letters, 44(8), 1533-1536 (2003).
Heck et al. "New scaffolds for supramolecular chemistry: upper-rim fully tethered 5-methyleneureido-5'-methyl-2,2'-bipyridyl cyclodextrins"; Chemistry—A European Journal, 8(11), 2438-2445(2002).
Reddy et al. "An efficient protocol for the reduction of azidocyclodextrins catalyzed by indium"; Indian Journal of Chemistry, Section B: Organic Chemistry Including Medicinal Chemistry, 41B(3), 645-646 (2002).
Velmurugan et al. "Optimization of the reversed-phase high-performance liquid chromatographic separation of the enantiomers of a cationic chiral drug (tolperisone) on a heptakis(6-azido-6-deoxy) perphenylcarbamated β-cyclodextrin column"; Chromatographia, 56(¾), 229-232(2002).
Chen et al. "Synthesis and chromatographic properties of a novel chiral stationary phase derived from heptakis(6-azido-6-deoxy-2,3-di-O-phenylcarbamoylated)-β-cyclodextrin immobilized onto amino-functionalized silica gel via multiple urea linkages"; Journal of Chromatography, 950(1-2), 65-74 (2002).
Ng et al. Enantiomer separation of flavor and fragrance compounds by liquid chromatography using novel urea-covalent bonded methylated β-cyclodextrins on silica;Journal of Chromatography, 968(1-2), 31-40 (2002).

Wagner et al. "Heptakis-6-(5-methylene-ureido-5'-methyl-2,2'-bithiazolyl)-cyclomaltoheptaose as a new fluorescent poly-dentate ligand"; Tetrahedron Letters, 42(31), 5207-5209 (2001).
Ravoo et al. "Supramolecular tapes formed by a catanionic cyclodextrin in water"; Chemical Communications (Cambridge, United Kingdom), (9), 827-828 (2001).
Busse et al. "An integrated optical Mach-Zehnder interferometer functionalized by β-cyclodextrin to monitor binding reactions"; Sensors and Actuators, B: Chemical, B80(2), 116-124 (2001).
Fulton et al. "Cyclodextrin-based carbohydrate clusters by amide bond formation" Israel Journal of Chemistry, 40(3-4), 325-333 (2000).
Charbonnier et al. "Heptakis-6-(5-methylene-ureido-5'-methyl-2,2'-bipyridinyl)-cyclomaltoheptaose as a new fluorescent lanthanide polydentate ligand"; Tetrahedron Letters, 40(21), 4047-4050 (1999).
Kraus et al. "Novel amphiphilic cyclodextrins: per[6-deoxy-6-(4,5-dicarboxy-1,2,3-triazol-1-yl)-2,3-di-O-methyl] derivatives"; Collection of Czechoslovak Chemical Communications, 63(4), 534-540 (1998).
Borrajo et al. "Derivatized cyclodextrins as peptidomimetics: influence on neurite growth"; Bioorganic & Medicinal Chemistry Letters, 7(9), 1185-1190 (1997).
Jimenez et al. "A mild one-step selective conversion of primary hydroxyl groups into azides in mono-and oligosaccharides"; Carbohydrate Research, 303(3), 367-372 (1997).
Kasselouri et al. "Inclusion capabilities of new amphiphilic cyclodextrins: a steady state fluorescence study, using pyrene"; Journal of Fluorescence, 7(1, Suppl.), 15S-23S (1997).
Gorin et al. "Efficient perfacial derivatization of cyclodextrins at the primary face"; Tetrahedron Letters, 37(27), 4647-4650 (1996).
Ashton et al. "Amino Acid Derivatives of β-Cyclodextrin"; Journal of Organic Chemistry, 61(3), 903-8 (1996).
Alexandre et al. "Scanning force microscopy investigation of amphiphilic cyclodextrin Langmuir-Blodgett films"; Thin Solid Films, 284-285, 765-768 (1996).
Kasselouri et al. "Mixed monolayers of amphiphilic cyclodextrins and phospholipids. I. Miscibility under dynamic conditions of compression"; Journal of Colloid and Interface Science, 180(2), 384-397 (1996).
Guillo et al. "Synthesis of symmetrical cyclodextrin derivatives bearing multiple charges"; Bulletin de la Societe Chimique de France, 132(8), 857-66 (1995).
Coleman et al. "Tailoring cyclodextrins for the construction of large scale molecular assemblies"; NATO ASI Series, Series C: Mathematical and Physical Sciences, 456, 77-97(1995).
Fernandez et al. "Isothiocyanates and cyclic thiocarbamates of α,α'-trehalose, sucrose, and cyclomaltooligosaccharides"; Carbohydrate Research, 268(1), 57-71 (1995).
Kaselouri et al. "Synthesis and self-organizational properties of the per-6-azido-6-deoxy-cyclodextrins"; Polish Journal of Chemistry, 67(11), 1981-5 (1993).
Parrot-Lopez et al. "Self-assembling systems of the amphiphilic cationic per-6-amino-β-cyclodextrin 2,3-di-O-alkyl ethers"; Journal of the American Chemical Society, 114(13), 5479-80 (1992).
Szurmai et al. "Halogen azide displacement to prepare some symmetrically substituted β-cyclodextrin derivatives"; Starch/Staerke, 42(11), 447-9 (1990).
Hattori et al. "Novel HPLC adsorbents by immobilization of modified cyclodextrins"; Journal of Inclusion Phenomena, 5(1), 73-6 (1987).
Hattori et al. "Novel high-performance liquid chromatographic adsorbents prepared by immobilization of modified cyclodextrins"; Journal of Chromatography, 355(2), 383-91 (1986).
Tsujihara et al. "Synthesis of amino derivatives of cycloheptaamylose having strong antimicrobial activities"; Chemistry Letters, (12), 1333-6 (1978).
Tsujihara et al. "The highly selective sulfonylation of cycloheptaamylose and syntheses of its pure amino derivatives"; Bulletin of the Chemical Society of Japan, 50(6), 1567-71 (1977).

\* cited by examiner

β-CYCLODEXTRIN DERIVATIVES AS ANTIBACTERIAL AGENTS

RELATED APPLICATIONS

This application claims the benefit of U.S. Provisional Patent Application Ser. No. 60/647,841, filed on Jan. 28, 2005, the contents of which are incorporated herein by reference in its entirety.

BACKGROUND OF THE INVENTION

1. Field of the Invention

The invention relates to development of new antibiotics against pathogenic bacteria.

2. Summary of the Related Art

Numerous bacteria are known to cause diseases in humans. Among these bacteria are *Enterococcus faecium, Eschericia coli, Pseudomonas aeruginosa, Bacillus atrophaeus, Staphylococcus aureus, Salmonella choleraesuis, Bacillus anthrasis*, and many others. A disturbing recent trend has been the development of resistance to existing antibiotics in numerous pathogenic bacteria. There is, therefore, a need for new antibiotics for which resistance has not yet emerged. Preferably, such antibiotics should be members of a new class of antibiotics, thus making evolutionary resistance to these antibiotics more difficult.

BRIEF SUMMARY OF THE INVENTION

The invention provides a new class of antibiotics to which pathogenic bacteria have not been exposed, and thus should not have developed resistance. This new class of antibiotics are derivatives of β-cyclodextrin (β-CD), which is a cyclic molecule comprising seven D-glucose units.

In a first aspect, the invention provides a compound having the formula

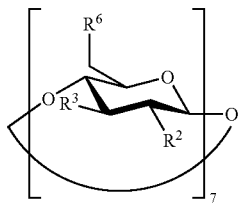

wherein $R_2$ is H, OH, OAc, O-lower alkyl, OMe, or $O(CH_2CH_2O)_n$; $R_3$ is H, OH, OAc, O-lower alkyl, OMe, $OSO_3Na$, or $NH_2$; and $R_6$ is N which is mono, di or tri-substituted with alkyl, aralkyl, aryl, heterocyclic ring or heterocyclic alkyl, and any of which substituents can be further substituted with N, O or S which can be further substituted with H, alkyl, aralkyl or aryl, wherein for each of $R_2$, $R_3$ and $R_6$ any one or more of the carbon atoms may be optionally replaced by S, N or O, and wherein $n$ is from about 1 to about 15, preferably from about 1 to about 10.

In a second aspect the invention provides pharmaceutical compositions. These compositions comprise one or more members of the compounds disclosed in the invention and a pharmaceutically acceptable carrier.

In a third aspect, the invention provides methods for using a compound or compounds having the formula:

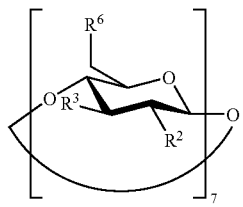

wherein $R_2$ is H, OH, OAc, OMe, O-lower alkyl, or $O(CH_2CH_2O)_n$; $R_3$ is H, OH, OAc, OMe, O-lower alkyl, $OSO_3Na$, or $NH_2$; and $R_6$ is H, $NH_2$, $S(CH_2)_mNH_2$, I, $N_3$, SH, lower alkyl, S-alkylguanidyl, O-alkylguanidyl, S-aminoalkyl, O-aminoalkyl, aminoalkyl, O-lower alkyl, aralkyl, aryl, heterocyclic ring(s), $OSO_3Na$ or N which is mono, di or tri-substituted with alkyl, aralkyl, aryl, heterocyclic ring or heterocyclic alkyl, and any of which substituents can be further substituted with N, O or S which can be further substituted with H, alkyl, aralkyl or aryl, wherein for each of $R_2$, $R_3$ and $R_6$ any one or more of the carbon atoms may be optionally replaced by S, N or O, and wherein $n$ is from about 1 to about 15, preferably from about 1 to about 10, and wherein $m$ is from about 1 to about 15, preferable from about 1 to about 10, as antimicrobial agents. In one embodiment of this aspect, the invention provides a method for inhibiting the growth of a bacterium. In a further embodiment of this aspect, the invention provides methods for treating a bacterial infection. In a further embodiment of this aspect, the invention provides methods for preventing a bacterial infection.

In a fourth aspect, the invention provides methods for potentiating the activity of antibiotics to inhibit the growth of a bacterium which are resistant to clinically used antibiotics, to treat or prevent an infection by these bacteria.

DETAILED DESCRIPTION OF THE PREFERRED EMBODIMENTS

The invention relates to development of new antibiotics against pathogenic bacteria. The invention provides a new class of antibiotics to which pathogenic bacteria have not been exposed, and thus should not have developed resistance. This new class of antibiotics are derivatives of β-cyclodextrin (β-CD), which is a cyclic molecule comprising seven D-glucose units.

In a first aspect, the invention provides a compound having the formula

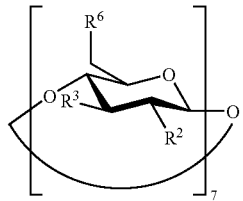

wherein $R_2$ is H, OH, OAc, O-lower alkyl, OMe, or $O(CH_2CH_2O)_n$; $R_3$ is H, OH, OAc, O-lower alkyl, OMe, $OSO_3Na$, or $NH_2$; and $R_6$ is N which is mono, di or tri-substituted with alkyl, aralkyl, aryl, heterocyclic ring or heterocyclic alkyl, and any of which substituents can be further substituted with N, O or S which can be further substituted with H, alkyl, aralkyl or aryl, wherein for each of $R_2$, $R_3$ and $R_6$ any one or more of the carbon atoms may be optionally replaced by S, N or O, and wherein $_n$ is from about 1 to about 15, preferably from about 1 to about 10.

In a second aspect the invention provides pharmaceutical compositions. These compositions comprise one or more members of the compounds disclosed in the invention and a pharmaceutically acceptable carrier.

As used herein, the term "physiologically acceptable" refers to a material that does not interfere with the effectiveness of the compounds of the first or third aspects of the invention and is compatible with a biological system such as a cell, cell culture, tissue, or organism. In certain embodiments, the biological system is a living organism, such as a mammal. In certain embodiments, the mammal is a human.

As used herein, the term "carrier" encompasses any excipient, diluent, filler, salt, buffer, stabilizer, solubilizer, lipid, or other material well known in the art for use in pharmaceutical formulations. It will be understood that the characteristics of the carrier, excipient, or diluent will depend on the route of administration for a particular application. The preparation of pharmaceutically acceptable formulations containing these materials is described in, e.g., Remington's Pharmaceutical Sciences, 18th Edition, ed. A. Gennaro, Mack Publishing Co., Easton, Pa., 1990, ISBN: 0-912734-04-3.

In a third aspect, the invention provides methods for using a compound or compounds of the first and second aspects of the invention as antimicrobial agents. In one embodiment of this aspect, the invention provides a method for inhibiting the growth of a bacterium. The method according to this embodiment of the invention comprises contacting the bacteria with one or more members of a compound having the formula

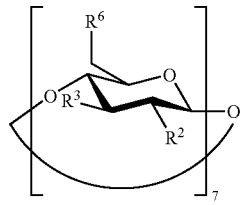

wherein $R_2$ is H, OH, OAc, OMe, O-lower alkyl, or $O(CH_2CH_2O)_n$; $R_3$ is H, OH, OAc, OMe, O-lower alkyl, $OSO_3Na$, or $NH_2$; and $R_6$ is H, $NH_2$, $S(CH_2)_m NH_2$, I, $N_3$, SH, lower alkyl, S-alkylguanidyl, O-alkylguanidyl, S-aminoalkyl, O-aminoalkyl, aminoalkyl, O-lower alkyl, aralkyl, aryl, heterocyclic ring(s), $OSO_3Na$ or N which is mono, di or tri-substituted with alkyl, aralkyl, aryl, heterocyclic ring or heterocyclic alkyl, and any of which substituents can be further substituted with N, O or S which can be further substituted with H, alkyl, aralkyl or aryl, wherein for each of $R_2$, $R_3$ and $R_6$ any one or more of the carbon atoms may be optionally replaced by S, N or O, and wherein $_n$ is from about 1 to about 15, preferably from about 1 to about 10, and wherein $_m$ is from about 1 to about 15, preferable from about 1 to about 10.

For purposes of the invention, the term "lower alkyl" means an alkyl group from 1 to 7 carbon atoms. The terms "alkyl" and "aryl" include alkyl or aryl groups which may be substituted or unsubstituted. Preferred substitutions include, without limitation, substitution with nitrogen containing moieties, including amino groups, which may be mono or disubstituted, preferably with alkyl or aryl groups. Also, for purposes of the invention the term "alkyl" includes chains of 1-7 atoms with one or more nitrogen atoms and the remainder carbon atoms.

In a further embodiment of this aspect, the invention provides methods for treating a bacterial infection. The method according to this embodiment of the invention comprises administering to a mammal with a bacterial infection one or more members of a compound having the formula

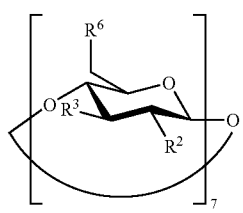

wherein $R_2$ is H, OH, OAc, OMe, O-lower alkyl, or $O(CH_2CH_2O)_n$; $R_3$ is H, OH, OAc, OMe, O-lower alkyl, $OSO_3Na$, or $NH_2$; and $R_6$ is H, $NH_2$, $S(CH_2)_m NH_2$, I, $N_3$, SH, lower alkyl, S-alkylguanidyl, O-alkylguanidyl, S-aminoalkyl, O-aminoalkyl, aminoalkyl, O-lower alkyl, aralkyl, aryl, heterocyclic ring(s), $OSO_3Na$ or N which is mono, di or tri-substituted with alkyl, aralkyl, aryl, heterocyclic ring or heterocyclic alkyl, and any of which substituents can be further substituted with N, O or S which can be further substituted with H, alkyl, aralkyl or aryl, wherein for each of $R_2$, $R_3$ and $R_6$ any one or more of the carbon atoms may be optionally replaced by S, N or O, and wherein $_n$ is from about 1 to about 15, preferably from about 1 to about 10, and wherein $_m$ is from about 1 to about 15, preferable from about 1 to about 10.

For purposes of the invention, the term "lower alkyl" means an alkyl group from 1 to 7 carbon atoms. The terms "alkyl" and "aryl" include alkyl or aryl groups which may be substituted or unsubstituted. Preferred substitutions include, without limitation, substitution with nitrogen containing moieties, including amino groups, which may be mono or disubstituted, preferably with alkyl or aryl groups. Also, for purposes of the invention the term "alkyl" includes chains of 1-7 atoms with one or more nitrogen atoms and the remainder carbon atoms.

In a further embodiment of this aspect, the invention provides methods for preventing a bacterial infection. The method according to this embodiment of the invention comprises administering to a mammal susceptible to a bacterial infection one or more members of a compound having the formula

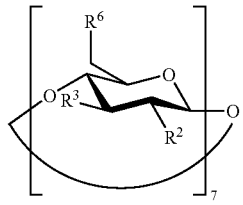

wherein $R_2$ is H, OH, OAc, OMe, O-lower alkyl, or $O(CH_2CH_2O)_n$; $R_3$ is H, OH, OAc, OMe, O-lower alkyl, $OSO_3Na$, or $NH_2$; and $R_6$ is H, $NH_2$, $S(CH_2)_m NH_2$, I, $N_3$, SH, lower alkyl, S-alkylguanidyl, O-alkylguanidyl, S-aminoalkyl, O-aminoalkyl, aminoalkyl, O-lower alkyl, aralkyl, aryl, heterocyclic ring(s), $OSO_3Na$ or N which is mono, di or tri-substituted with alkyl, aralkyl, aryl, heterocyclic ring or heterocyclic alkyl, and any of which substituents can be further substituted with N, O or S which can be further substituted with H, alkyl, aralkyl or aryl, wherein for each of $R_2$, $R_3$ and $R_6$ any one or more of the carbon atoms may be optionally replaced by S, N or O, and wherein $_n$ is from about 1 to about 15, preferably from about 1 to about 10, and wherein $_m$ is from about 1 to about 15, preferable from about 1 to about 10.

For purposes of the invention, the term "lower alkyl" means an alkyl group from 1 to 7 carbon atoms. The terms "alkyl" and "aryl" include alkyl or aryl groups which may be substituted or unsubstituted. Preferred substitutions include, without limitation, substitution with nitrogen containing moieties, including amino groups, which may be mono or disubstituted, preferably with alkyl or aryl groups. Also, for purposes of the invention the term "alkyl" includes chains of 1-7 atoms with one or more nitrogen atoms and the remainder carbon atoms.

In the methods according to this aspect of the invention the bacteria is in a mammal. Preferably, the mammal is a human.

In the methods according to this aspect of the invention, administration of the compound can be by any suitable route, including, without limitation, parenteral, oral, sublingual, transdermal, topical, intranasal, aerosol, intraocular, intratracheal, intrarectal or vaginal. Administration of the therapeutic compositions can be carried out using known procedures at dosages and for periods of time effective to reduce symptoms or surrogate markers of the infection. A doctor can determine the appropriate dose to administer or therapeutic protocol useful for preventing or preventing a bacterial infection. It may be desirable to administer simultaneously, or sequentially a therapeutically effective amount of one or more of the therapeutic compositions of the invention to an individual as a single treatment episode.

In a fourth aspect, the invention provides methods for potentiating the activity of antibiotics to inhibit the growth of a bacterium which are resistant to clinically used antibiotics, to treat or prevent an infection by these bacteria. The methods according to this aspect of the invention comprise contacting the bacterium with said antibiotic and one or more members of a compound having the formula

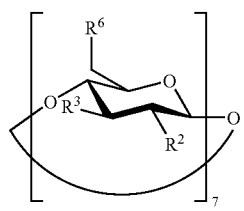

wherein $R_2$ is H, OH, OAc, OMe, O-lower alkyl, or $O(CH_2CH_2O)_n$; $R_3$ is H, OH, OAc, OMe, O-lower alkyl, $OSO_3Na$, or $NH_2$; and $R_6$ is H, $NH_2$, $S(CH_2)_mNH_2$, I, $N_3$, SH, lower alkyl, S-alkylguanidyl, O-alkylguanidyl, S-aminoalkyl, O-aminoalkyl, aminoalkyl, O-lower alkyl, aralkyl, aryl, heterocyclic ring(s), $OSO_3Na$ or N which is mono, di or tri-substituted with alkyl, aralkyl, aryl, heterocyclic ring or heterocyclic alkyl, and any of which substituents can be further substituted with N, O or S which can be further substituted with H, alkyl, aralkyl or aryl, wherein for each of $R_2$, $R_3$ and $R_6$ any one or more of the carbon atoms may be optionally replaced by S, N or O, and wherein $_n$ is from about 1 to about 15, preferably from about 1 to about 10, and wherein $_m$ is from about 1 to about 15, preferable from about 1 to about 10.

For purposes of the invention, the term "lower alkyl" means an alkyl group from 1 to 7 carbon atoms. The terms "alkyl" and "aryl" include alkyl or aryl groups which may be substituted or unsubstituted. Preferred substitutions include, without limitation, substitution with nitrogen containing moieties, including amino groups, which may be mono or disubstituted, preferably with alkyl or aryl groups. Also, for purposes of the invention the term "alkyl" includes chains of 1-7 atoms with one or more nitrogen atoms and the remainder carbon atoms.

For purposes of the invention, the term "resistant" or "resistance" to a bacterium or bacterial infection to an antibiotic includes a complete resistance to the antibiotic or a partial resistance which is defined herein as a circumstance in which the MIC of an antibiotic toward the organism in question has increased.

For purposes herein, potentiation may be defined as a circumstance in which a compound substantially lowers the MIC of an antibacterial agent toward one or more organisms. It includes the case in which it effectively restores the therapeutic utility of an antibacterial agent whose utility has been compromised by bacterial resistance.

In any of the methods according to the invention, one or more members of compounds of the invention can be administered in combination with any other antibiotic useful for treating the disease or condition that does not diminish the antimicrobial effect of the compound. For purposes of this aspect of the invention, the term "in combination with" means in the course of treating the same disease in the same patient, and includes administering the compound and an antibiotic in any order, including simultaneous administration, as well as any temporally spaced order, for example, from sequentially with one immediately following the other to up to several days apart. Such combination treatment may also include more than a single administration of the compound, and independently the antibiotic. The administration of the compound and antibiotic may be by the same or different routes.

In the methods according to this aspect of the invention the bacteria is in a mammal. Preferably, the mammal is a human.

In the methods according to this aspect of the invention, administration of the compound can be by any suitable route, including, without limitation, parenteral, oral, sublingual, transdermal, topical, intranasal, aerosol, intraocular, intratracheal, intrarectal or vaginal. Administration of the therapeutic compositions can be carried out using known procedures at dosages and for periods of time effective to reduce symptoms or surrogate markers of the infection. A doctor can determine the appropriate dose to administer or therapeutic protocol useful for preventing or preventing a bacterial infection. It may be desirable to administer simultaneously, or sequentially a therapeutically effective amount of one or more of the therapeutic compositions of the invention to an individual as a single treatment episode.

In certain aspects of the methods according to the invention, it is desirable to have antibiotics with a relatively broad spectrum, so that a variety of different bacterial infection can be treated. In other aspects, such as protection against bioterrorism, it may be desirable to have antibiotics with a narrow spectrum, specific for likely bioterrorism organisms, so that protection from the bacteria may be obtained while preserving the normal flora in the body. The invention provides methods for achieving each of these goals.

The following examples are intended to further illustrate certain particularly preferred embodiments of the invention and are not intended to limit the scope of the invention.

EXAMPLE 1

Bacterial Growth Standardization

One to three colonies of bacteria were picked from an Mueller-Hinton or Brain Heart infusion agar plate (depending on the bacterial strain) and transferred to 3 ml Mueller-Hinton broth or Brain Heart infusion media (depending on the bacterial strain). Bacteria were allowed to grow for 2-4 hours in an incubator at 37° C. Bacteria-inoculated media were dispersed in 0.9% saline to match McFarland standard density. 100 µl standardized inoculation was added to 20 ml media (dilution 1). 10 µl of the new dilution was added to 990 µl media and mixed (dilution 2). 10 µl of dilution 2 was spread on an agar plate and allowed to grow overnight. Colonies were then plated.

EXAMPLE 2

Bacterial Panel Testing

Test compound was diluted to 10 µg/ml in dimethylsulfoxide. Four µl of diluted test compound was loaded into column 2 of a 96 well NUNC microplate, as shown in Table 1 below. Four µl of Rifampicin antibiotic was loaded into row H, column 2.

TABLE 1

96 well NUNC microplate set-up, Concentration in µg/ml

|   | 1 | 2 | 3 | 4 | 5 | 6 | 7 | 8 | 9 | 10 | 11 | 12 |
|---|---|---|---|---|---|---|---|---|---|----|----|----|
| A | 0 | 200 | 100 | 50 | 25 | 12.5 | 6.25 | 3.12 | 1.56 | 0.78 | 0.39 | 0.20 |
| B | 0 | 200 | 100 | 50 | 25 | 12.5 | 6.25 | 3.12 | 1.56 | 0.78 | 0.39 | 0.20 |
| C | 0 | 200 | 100 | 50 | 25 | 12.5 | 6.25 | 3.12 | 1.56 | 0.78 | 0.39 | 0.20 |
| D | 0 | 200 | 100 | 50 | 25 | 12.5 | 6.25 | 3.12 | 1.56 | 0.78 | 0.39 | 0.20 |
| E | 0 | 200 | 100 | 50 | 25 | 12.5 | 6.25 | 3.12 | 1.56 | 0.78 | 0.39 | 0.20 |
| F | 0 | 200 | 100 | 50 | 25 | 12.5 | 6.25 | 3.12 | 1.56 | 0.78 | 0.39 | 0.20 |
| G | 0 | 200 | 100 | 50 | 25 | 12.5 | 6.25 | 3.12 | 1.56 | 0.78 | 0.39 | 0.20 |
| H rifampicin | 0 | 200 | 100 | 50 | 25 | 12.5 | 6.25 | 3.12 | 1.56 | 0.78 | 0.39 | 0.20 |

All wells were then filled with 100 µl of inoculated media (dilution 1 from Example 1). A further 100 µl of the inoculated media was then added to column 2 and the contents are pipetted to thoroughly mix the contents. A full 100 µl was then transferred from column 2 and mixed into column 3. This process was continued from left to right until columns 2-12 were serially diluted, and the final draw from column 12 was discarded. The plates were covered with 3M sealing tape (plates containing *Enterococcus faecium* were sealed with Air Pore sealing tape) and allowed to grow for 20-24 hours. Cytotoxic wells (clear wells) are then scored and the potency of the compound was determined. The results are shown in Table 2 below. These results show that while some compounds were inactive, others demonstrated either broad spectrum or narrow spectrum activity.

TABLE 2

Activity of test compounds (MICs in µg/mL)

| Compound | PA | SA | SC | EC | BA | EF | Mammalian Cytotoxicity* IC50 (µg/mL) |
|---|---|---|---|---|---|---|---|
| 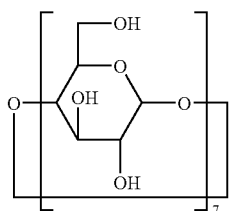 PP5000 | >200 | >200 | >200 | >200 | >200 | >200 | |

TABLE 2-continued
Activity of test compounds (MICs in μg/mL)
| Compound | PA | SA | SC | EC | BA | EF | Mammalian Cytotoxicity* IC50 (μg/mL) |
|---|---|---|---|---|---|---|---|
| 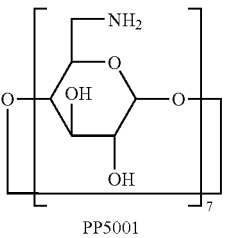 PP5001 | 6.25-3.12 | >200 | >200 | 200-100 | 100-50 | >200 | 720 |
| 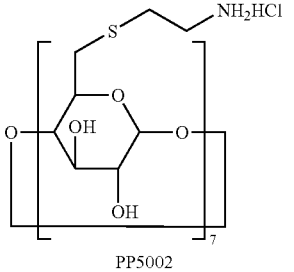 PP5002 | >200 | >200 | >200 | >200 | 12.5-6.25 | >200 | 829 |
| 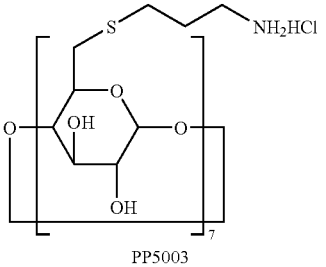 PP5003 | >200 | >200 | >200 | 100-50 | 3.12-1.56 | >200 | 191 |
| 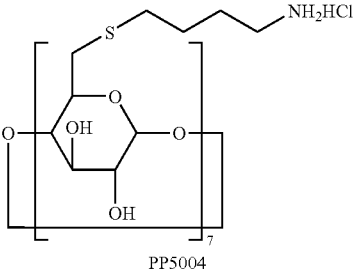 PP5004 | >200 | >200 | >200 | >200 | 1.56-0.78 | >200 | 198 |
| 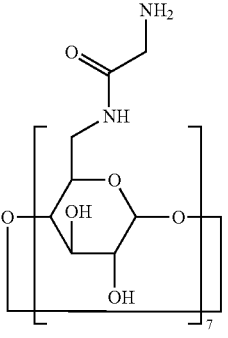 PP5005 | >200 | >200 | >200 | >200 | 200-100 | >200 | 690 |

TABLE 2-continued
Activity of test compounds (MICs in μg/mL)
| Compound | PA | SA | SC | EC | BA | EF | Mammalian Cytotoxicity* IC50 (μg/mL) |
|---|---|---|---|---|---|---|---|
| 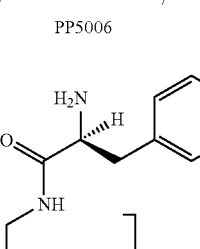 PP5006 | >200 | >200 | >200 | >200 | 50-25 | >200 | 215 |
| 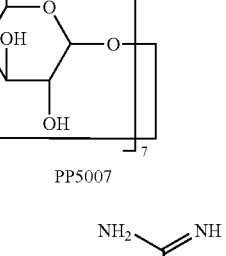 PP5007 | >200 | >200 | >200 | >200 | 25-12.5 | >200 | >2000 |
| 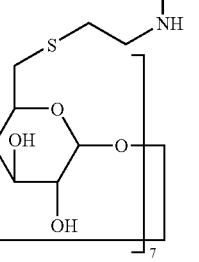 PP5008 | >200 | >200 | >200 | >200 | 25-12.5 | >200 | 510 |
| 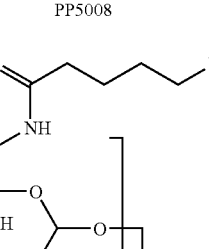 PP5009 | >200 | >200 | >200 | >200 | 200-100 | >200 | 755 |

TABLE 2-continued

Activity of test compounds (MICs in μg/mL)

| Compound | PA | SA | SC | EC | BA | EF | Mammalian Cytotoxicity* IC50 (μg/mL) |
|---|---|---|---|---|---|---|---|
| PP5010 | >200 | 100-50 | >200 | >200 | 200-100 | >200 | 780 |
| PP5011 | >200 | 3.12-1.56 | 50-25 | 25-12.5 | 1.56-0.78 | 50-25 | 840 |
| PP5012 | >200 | >200 | >200 | >200 | >200 | >200 | 193 |
| PP5013 | >200 | >200 | >200 | >200 | >200 | >200 | 144 |

TABLE 2-continued

Activity of test compounds (MICs in µg/mL)

| Compound | PA | SA | SC | EC | BA | EF | Mammalian Cytotoxicity* IC50 (µg/mL) |
|---|---|---|---|---|---|---|---|
| PP5014 | >200 | >200 | >200 | >200 | <0.2 | >200 | |
| PP5015 | >200 | 50-25 | >200 | >200 | 100-50 | >200 | 2116 |
| PP5016 | >200 | >200 | >200 | >200 | 200-100 | >200 | |
| PP5017 | >200 | >200 | >200 | >200 | >200 | >200 | |

TABLE 2-continued

Activity of test compounds (MICs in µg/mL)

| Compound | PA | SA | SC | EC | BA | EF | Mammalian Cytotoxicity* IC50 (µg/mL) |
|---|---|---|---|---|---|---|---|
| PP5018 | >200 | >200 | >200 | >200 | 100-50 | >200 | |
| PP5019 | >200 | >200 | >200 | >200 | 25-12.5 | >200 | 524 |
| PP5020 | >200 | >200 | >200 | >200 | 200-100 | >200 | |
| PP5021 | >200 | >200 | >200 | >200 | >200 | >200 | |

TABLE 2-continued

Activity of test compounds (MICs in μg/mL)

| Compound | PA | SA | SC | EC | BA | EF | Mammalian Cytotoxicity* IC50 (μg/mL) |
|---|---|---|---|---|---|---|---|
| PP5026 | >200 | >200 | >200 | >200 | 50-25 | >200 | |
| PP5027 | >200 | >200 | 25-12.5 | 50-25 | 1.56-0.78 | >200 | 321 |
| PP5028 | >200 | >200 | >200 | >200 | 25-12.5 | >200 | 2990 |
| PP5029 | >200 | >200 | >200 | >200 | >200 | >200 | |

TABLE 2-continued

Activity of test compounds (MICs in μg/mL)

| Compound | PA | SA | SC | EC | BA | EF | Mammalian Cytotoxicity* IC50 (μg/mL) |
|---|---|---|---|---|---|---|---|
| PP5030 | >200 | >200 | >200 | >200 | >200 | >200 | |
| PP5031 | >200 | >200 | >200 | >200 | 12.5-6.25 | >200 | |
| PP5032 | >200 | >200 | >200 | >200 | >200 | >200 | |
| PP5033 | >200 | >200 | >200 | >200 | >200 | >200 | |

TABLE 2-continued
Activity of test compounds (MICs in µg/mL)
| Compound | PA | SA | SC | EC | BA | EF | Mammalian Cytotoxicity* IC50 (µg/mL) |
|---|---|---|---|---|---|---|---|
| 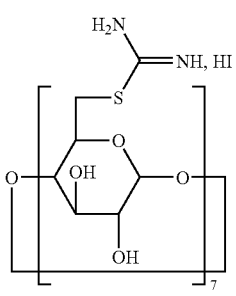 PP5035 | >200 | >200 | >200 | >200 | 25-12.5 | >200 | 480 |
| 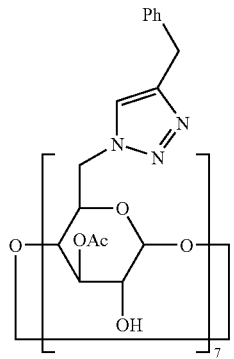 PP5036 | >200 | >200 | >200 | >200 | >200 | >200 | |
| 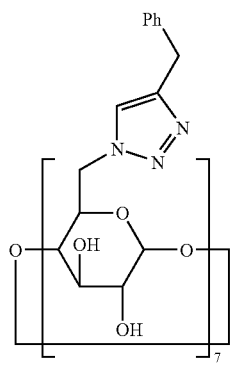 PP5037 | >200 | >200 | >200 | >200 | >200 | >200 | |
| 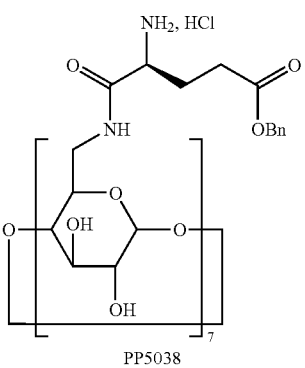 PP5038 | >200 | >200 | >200 | >200 | 200-100 | >200 | |

TABLE 2-continued

Activity of test compounds (MICs in µg/mL)

| Compound | PA | SA | SC | EC | BA | EF | Mammalian Cytotoxicity* IC50 (µg/mL) |
|---|---|---|---|---|---|---|---|
| PP5039 | >200 | >200 | >200 | >200 | >200 | >200 | |
| PP5040 | >200 | >200 | 100-50 | 50-25 | 25-12.5 | >200 | |
| PP5041 | 100-50 | >200 | >200 | >200 | 50-25 | >200 | 860 |
| PP5042 | >200 | >200 | >200 | >200 | >200 | >200 | |

TABLE 2-continued
Activity of test compounds (MICs in μg/mL)
| Compound | PA | SA | SC | EC | BA | EF | Mammalian Cytotoxicity* IC50 (μg/mL) |
|---|---|---|---|---|---|---|---|
| 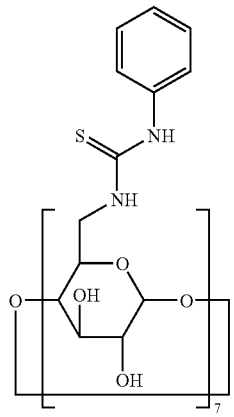 PP5043 | >200 | >200 | >200 | >200 | >200 | >200 | |
| 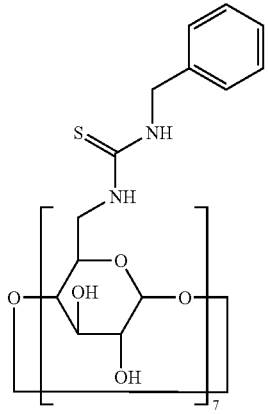 PP5044 | >200 | >200 | >200 | >200 | >200 | >200 | |
| 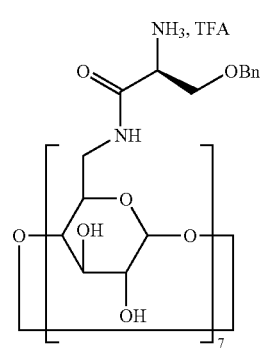 PP5046 | >200 | 200-100 | 100-50 | 200-100 | 12.5-6.25 | — | |

TABLE 2-continued

Activity of test compounds (MICs in µg/mL)

| Compound | PA | SA | SC | EC | BA | EF | Mammalian Cytotoxicity* IC50 (µg/mL) |
|---|---|---|---|---|---|---|---|
| PP5047 | >200 | >200 | >200 | >200 | 50-25 | — | |
| PP5048 | >200 | 50-25 | 100-50 | >200 | 6.25-3.12 | — | |
| PP5049 | >200 | >200 | >200 | >200 | 100-50 | | |
| PP5050 | >200 | >200 | >200 | >200 | >200 | >200 | |

TABLE 2-continued

Activity of test compounds (MICs in μg/mL)

| Compound | PA | SA | SC | EC | BA | EF | Mammalian Cytotoxicity* IC50 (μg/mL) |
|---|---|---|---|---|---|---|---|
| PP5051 | >200 | >200 | >200 | >200 | 12.5-6.25 | >200 | |
| PP5052 | >200 | >200 | >200 | >200 | 25-12.5 | >200 | |
| PP5053 | >200 | >200 | >200 | >200 | >200 | >200 | |
| PP5054 | >200 | >200 | >200 | >200 | >200 | >200 | |

TABLE 2-continued

Activity of test compounds (MICs in μg/mL)

| Compound | PA | SA | SC | EC | BA | EF | Mammalian Cytotoxicity* IC50 (μg/mL) |
|---|---|---|---|---|---|---|---|
| PP5055 | >200 | >200 | >200 | >200 | >200 | >200 | |
| PP5056 | >200 | >200 | >200 | >200 | >200 | >200 | |
| PP5057 | 200-100 | >200 | >200 | >200 | >200 | >200 | |

TABLE 2-continued
| | Activity of test compounds (MICs in μg/mL) | | | | | | Mammalian Cytotoxicity* |
|---|---|---|---|---|---|---|---|
| Compound | PA | SA | SC | EC | BA | EF | IC50 (μg/mL) |
| 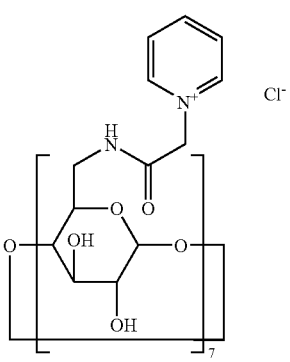 PP5058 | >200 | >200 | >200 | >200 | 200-100 | >200 | |
| 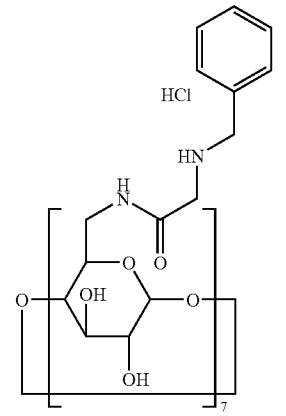 PP5059 | >200 | >200 | >200 | >200 | 100-50 | >200 | |
| 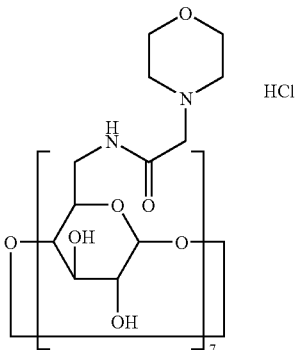 PP5060 | >200 | >200 | >200 | >200 | >200 | >200 | |

TABLE 2-continued

Activity of test compounds (MICs in μg/mL)

| Compound | PA | SA | SC | EC | BA | EF | Mammalian Cytotoxicity* IC50 (μg/mL) |
|---|---|---|---|---|---|---|---|
| PP5061 | >200 | >200 | >200 | >200 | >200 | >200 | |
| PP5062 | >200 | >200 | >200 | >200 | 200-100 | >200 | |
| PP5063 | >200 | >200 | >200 | >200 | >200 | >200 | |

TABLE 2-continued

Activity of test compounds (MICs in µg/mL)

| Compound | PA | SA | SC | EC | BA | EF | Mammalian Cytotoxicity* IC50 (µg/mL) |
|---|---|---|---|---|---|---|---|
| PP5064 | >200 | 200-100 | 100-50 | 200-100 | 100-50 | >200 | |
| PP5065 | >200 | >200 | >200 | >200 | >200 | >200 | |
| PP5066 | >200 | >200 | >200 | >200 | >200 | >200 | |
| PP5067 | >200 | >200 | >200 | >200 | >200 | >200 | |

TABLE 2-continued

| | Activity of test compounds (MICs in µg/mL) | | | | | | Mammalian Cytotoxicity* |
|---|---|---|---|---|---|---|---|
| Compound | PA | SA | SC | EC | BA | EF | IC50 (µg/mL) |
| PP5068 | >200 | >200 | >200 | >200 | >200 | >200 | |
| PP5069 | >200 | >200 | >200 | >200 | >200 | >200 | |
| PP5070 | >200 | 3.12-1.56 | 25-12.5 | 12.5-6.25 | 1.56-0.78 | 6.25-3.12 | 43 |

TABLE 2-continued
Activity of test compounds (MICs in µg/mL)
| Compound | PA | SA | SC | EC | BA | EF | Mammalian Cytotoxicity* IC50 (µg/mL) |
|---|---|---|---|---|---|---|---|
| 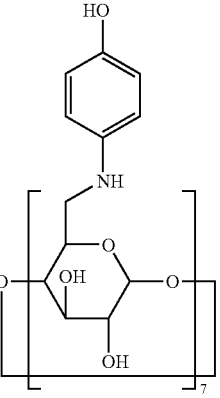 PP5071 | >200 | >200 | >200 | >200 | >200 | >200 |  |
| 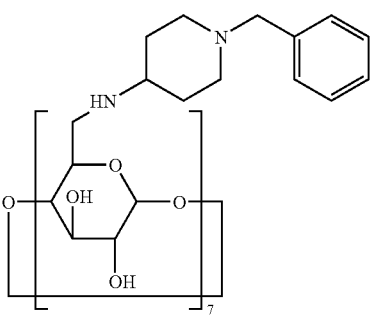 PP5072 | >200 | 6.25-3.12 | 200-100 | 100-50 | 1.56-0.78 | 6.25-3.12 | 127 |
| 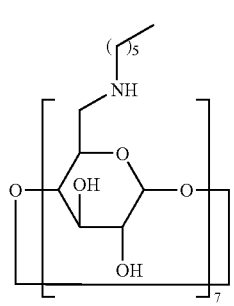 PP5073 | >200 | 3.12-1.56 | 50-25 | 50-25 | 1.56-0.78 | 6.35-3.12 | 129 |
| 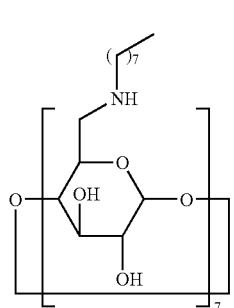 PP5074 | >200 | 6.25-3.12 | 50-25 | 100-50 | 6.25-3.12 | 6.25-3.12 | 123 |

TABLE 2-continued

Activity of test compounds (MICs in μg/mL)

| Compound | PA | SA | SC | EC | BA | EF | Mammalian Cytotoxicity* IC50 (μg/mL) |
|---|---|---|---|---|---|---|---|
| PP5075 | >200 | 100-50 | >200 | >200 | 50-25 | 200-100 | |
| PP5076 | >200 | 12.5-6.25 | >200 | >200 | 6.25-3.12 | 12.5-6.25 | 398 |
| PP5077 | >200 | >200 | >200 | >200 | >200 | >200 | |

TABLE 2-continued

Activity of test compounds (MICs in µg/mL)

| Compound | PA | SA | SC | EC | BA | EF | Mammalian Cytotoxicity* IC50 (µg/mL) |
|---|---|---|---|---|---|---|---|
| PP5078 | >200 | >200 | >200 | >200 | 100-50 | >200 | |
| PP5079 | >200 | 25-12.5 | >200 | >200 | 12.5-6.25 | 25-12.5 | 317 |
| PP5080 | >200 | >200 | >200 | >200 | 12.5-6.25 | 50-25 | |

TABLE 2-continued
Activity of test compounds (MICs in µg/mL)
| Compound | PA | SA | SC | EC | BA | EF | Mammalian Cytotoxicity* IC50 (µg/mL) |
|---|---|---|---|---|---|---|---|
| 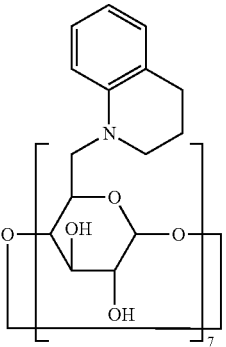 PP5084 | >200 | 200-100 | >200 | >200 | 50-25 | >200 | |
| 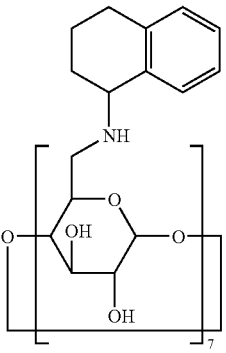 PP5085 | >200 | 12.5-6.25 | 200-100 | >200 | 6.25-3.12 | >200 | |
| 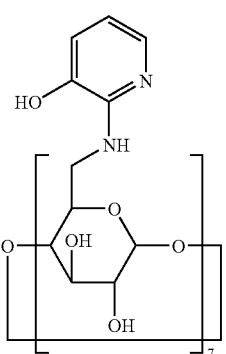 PP5086 | >200 | 50-25 | >200 | >200 | 50-25 | 100-50 | |

TABLE 2-continued
Activity of test compounds (MICs in μg/mL)
| Compound | PA | SA | SC | EC | BA | EF | Mammalian Cytotoxicity* IC50 (μg/mL) |
|---|---|---|---|---|---|---|---|
| 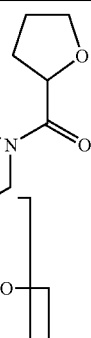 PP5087 | >200 | >200 | >200 | >200 | >200 | >200 | |
| 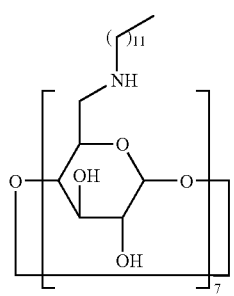 PP5088 | >200 | 200-100 | >200 | >200 | >200 | >200 | |
| 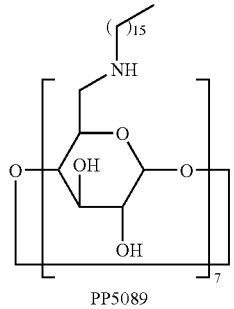 PP5089 | >200 | 200-100 | >200 | >200 | >200 | >200 | |
| 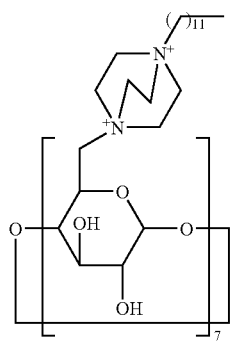 PP5093 | >200 | 6.25-3.12 | >200 | >200 | 3.12-1.56 | 12.5-6.25 | |

TABLE 2-continued

| | Activity of test compounds (MICs in µg/mL) | | | | | | |
|---|---|---|---|---|---|---|---|
| Compound | PA | SA | SC | EC | BA | EF | Mammalian Cytotoxicity* IC50 (µg/mL) |
| PP5094 | >200 | 3.12-1.56 | 100-50 | 100-50 | 3.12-1.56 | 1.56-0.78 | |
| PP5096 | >200 | >200 | >200 | >200 | >200 | >200 | |
| PP5097 | >200 | 12.5-6.25 | >200 | >200 | 6.25-3.12 | 100-50 | |

TABLE 2-continued

Activity of test compounds (MICs in μg/mL)

| Compound | PA | SA | SC | EC | BA | EF | Mammalian Cytotoxicity* IC50 (μg/mL) |
|---|---|---|---|---|---|---|---|
| PP5098 | >200 | 3.12-1.56 | >200 | 100-50 | 1.56-0.78 | 25-12.5 | 378 |
| PP5099 | >200 | 25-12.5 | >200 | >200 | 12.5-6.25 | 50-25 | |
| PP5100 | 100-50 | 50-25 | 100-50 | 100-50 | 50-25 | >200 | |

TABLE 2-continued

Activity of test compounds (MICs in µg/mL)

| Compound | PA | SA | SC | EC | BA | EF | Mammalian Cytotoxicity* IC50 (µg/mL) |
|---|---|---|---|---|---|---|---|
| PP5101 | >200 | >200 | >200 | >200 | >200 | >200 | |
| PP5102 | >200 | 200-100 | >200 | >200 | 100-50 | >200 | |
| PP5103 | >200 | 12.5-6.25 | >200 | >200 | 12.5-6.25 | 50-25 | |

TABLE 2-continued

Activity of test compounds (MICs in µg/mL)

| Compound | PA | SA | SC | EC | BA | EF | Mammalian Cytotoxicity* IC50 (µg/mL) |
|---|---|---|---|---|---|---|---|
| PP5104 | >200 | 25-12.5 | >200 | >200 | 25-12.5 | >200 | |
| PP5105 | >200 | 3.12-1.56 | >200 | 50-25 | 1.56-0.78 | 12.5-6.25 | 376 |
| PP5106 | >200 | >200 | >200 | >200 | 200-100 | >200 | |

TABLE 2-continued

Activity of test compounds (MICs in µg/mL)

| Compound | PA | SA | SC | EC | BA | EF | Mammalian Cytotoxicity* IC50 (µg/mL) |
|---|---|---|---|---|---|---|---|
| PP5107 | >200 | 12.5-6.25 | 25-12.5 | 25-12.5 | 6.25-3.12 | 25-12.5 | 105 |
| PP5108 | >200 | 12.5-6.25 | >200 | 100-50 | 6.25-3.12 | 25-12.5 | |
| PP5109 | >200 | 12.5-6.25 | >200 | >200 | 12.5-6.25 | 25-12.5 | |
| PP5110 | >200 | 12.5-6.25 | >200 | >200 | 6.25-3.12 | 25-12.5 | |

TABLE 2-continued
Activity of test compounds (MICs in µg/mL)
| Compound | PA | SA | SC | EC | BA | EF | Mammalian Cytotoxicity* IC50 (µg/mL) |
|---|---|---|---|---|---|---|---|
| PP5111 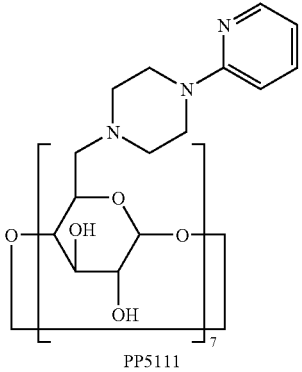 | >200 | >200 | >200 | >200 | >200 | >200 | |
| PP5112 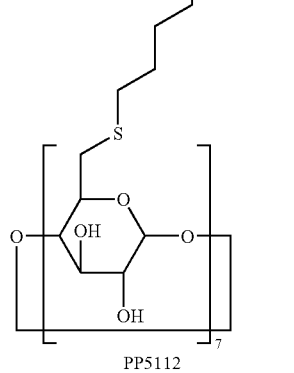 | >200 | >200 | >200 | >200 | 12.5-6.25 | >200 | |
| PP5113 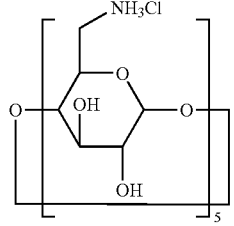 | 100-50 | >200 | >200 | >200 | >200 | >200 | 109.3 |
| PP5114 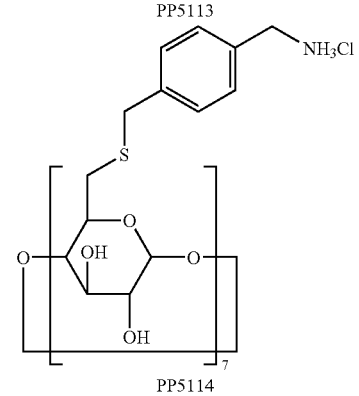 | 100-50 | >200 | 200-100 | 50-25 | 6.25-3.12 | >200 | 56.2 |

TABLE 2-continued
Activity of test compounds (MICs in µg/mL)
| Compound | PA | SA | SC | EC | BA | EF | Mammalian Cytotoxicity* IC50 (µg/mL) |
|---|---|---|---|---|---|---|---|
| 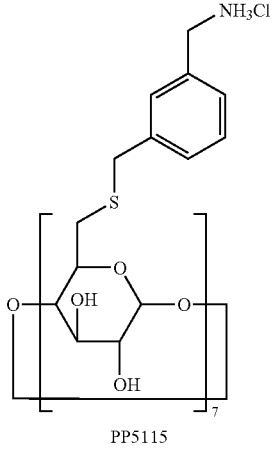 PP5115 | 200-100 | 200-100 | >200 | 50-25 | 6.25-3.12 | >200 | 54.3 |
| 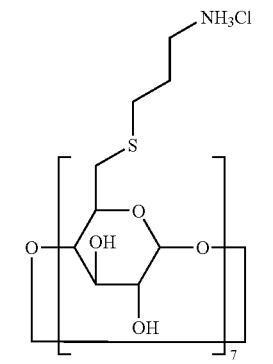 PP5116 | >200 | >200 | >200 | >200 | >200 | >200 | |
| 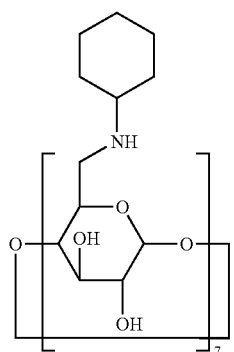 PP5117 | >200 | 6.25-3.12 | >200 | 200-100 | 3.12-1.56 | 100-50 | 373 |

TABLE 2-continued

Activity of test compounds (MICs in μg/mL)

| Compound | PA | SA | SC | EC | BA | EF | Mammalian Cytotoxicity* IC50 (μg/mL) |
|---|---|---|---|---|---|---|---|
| PP5118 | >200 | 6.25-3.12 | 200-100 | 100-50 | 3.12-1.56 | 100-50 | 282 |
| PP5119 | >200 | >200 | >200 | >200 | 200-100 | >200 | |
| PP5120 | >200 | >200 | >200 | >200 | >200 | >200 | |

TABLE 2-continued
| | Activity of test compounds (MICs in µg/mL) | | | | | | |
|---|---|---|---|---|---|---|---|
| Compound | PA | SA | SC | EC | BA | EF | Mammalian Cytotoxicity* IC50 (µg/mL) |
| 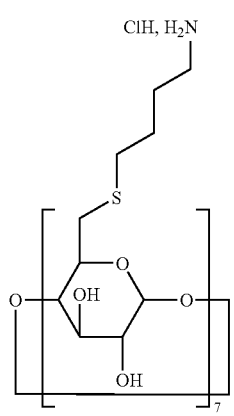  PP5121 | >200 | >200 | >200 | >200 | 50-25 | >200 | 589 |
| 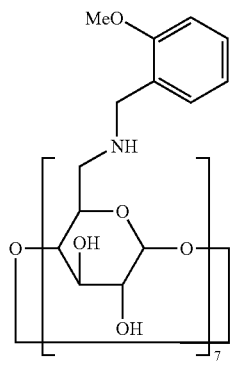  PP5122 | >200 | 6.25-3.12 | 25-12.5 | 25-12.5 | 3.12-1.56 | 50-25 | 297 |
| 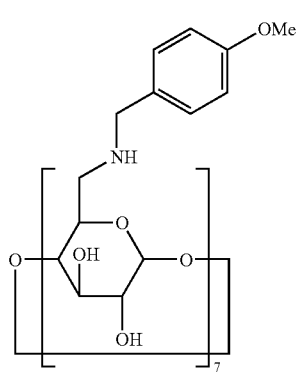  PP5123 | >200 | 6.25-3.12 | >200 | 200-100 | 3.12-1.56 | 200-100 | 297 |

TABLE 2-continued

Activity of test compounds (MICs in μg/mL)

| Compound | PA | SA | SC | EC | BA | EF | Mammalian Cytotoxicity* IC50 (μg/mL) |
|---|---|---|---|---|---|---|---|
| PP5124 | 200-100 | >200 | >200 | >200 | 50-25 | >200 | |
| PP5125 | >200 | 3.12-1.56 | 100-50 | 50-25 | 3.12-1.56 | 12.5-6.25 | |
| PP5126 | >200 | 12.5-6.25 | 100-50 | 200-100 | 25-12.5 | 12.5-6.25 | |

TABLE 2-continued

| Compound | Activity of test compounds (MICs in μg/mL) | | | | | | Mammalian Cytotoxicity* IC50 (μg/mL) |
| --- | --- | --- | --- | --- | --- | --- | --- |
| | PA | SA | SC | EC | BA | EF | |
| PP5127 | >200 | 6.25-3.12 | 100-50 | 200-100 | 12.5-6.25 | 6.25-3.12 | |
| PP5128 | >200 | >200 | >200 | 100-50 | 50-25 | >200 | |
| PP5129 | >200 | 200-100 | >200 | >200 | 12.5-6.25 | >200 | |

TABLE 2-continued
| | Activity of test compounds (MICs in μg/mL) | | | | | | Mammalian Cytotoxicity* |
|---|---|---|---|---|---|---|---|
| Compound | PA | SA | SC | EC | BA | EF | IC50 (μg/mL) |
| 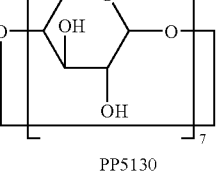 PP5130 | >200 | 6.25-3.12 | >200 | 100-50 | 6.25-3.12 | 6.25-3.12 | |
| 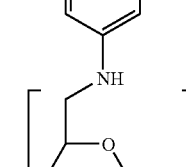 PP5131 | >200 | 12.5-6.25 | >200 | >200 | 12.5-6.25 | 12.5-6.25 | |
| 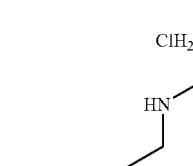 PP5132 | >200 | 100-50 | >200 | >200 | 50-25 | >200 | |

TABLE 2-continued
| Compound | Activity of test compounds (MICs in µg/mL) | | | | | | Mammalian Cytotoxicity* IC50 (µg/mL) |
| --- | --- | --- | --- | --- | --- | --- | --- |
|  | PA | SA | SC | EC | BA | EF |  |
| 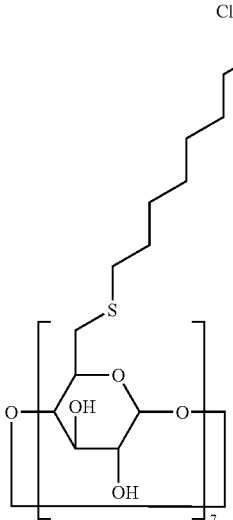 PP5133 | 6.25-3.12 | 25-12.5 | 3.12-1.56 | 3.12-1.56 | 1.56-0.78 | | 100-50 |
| 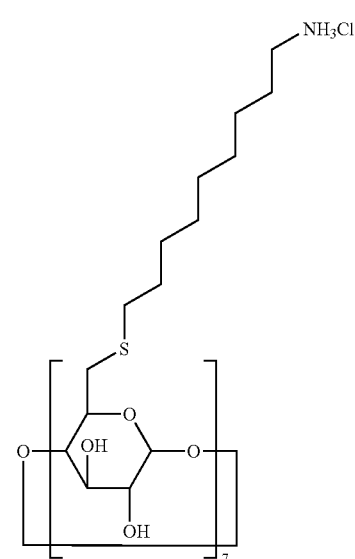 PP5134 | 25-12.5 | 12.5-6.25 | 6.25-3.12 | 6.25-3.12 | 6.25-3.12 | 12.5-6.25 | |

TABLE 2-continued

| | Activity of test compounds (MICs in μg/mL) | | | | | | Mammalian Cytotoxicity* |
|---|---|---|---|---|---|---|---|
| Compound | PA | SA | SC | EC | BA | EF | IC50 (μg/mL) |
| PP5135 | 100-50 | 25-12.5 | 25-12.5 | 25-12.5 | 12.5-6.25 | 50-25 | 32.4 |
| PP5136 | >200 | 12.5-6.25 | 200-100 | 200-100 | 3.12-1.56 | >200 | |
| PP5137 | 12.5-6.25 | 12.5-6.25 | 200-100 | >200 | 12.5-6.25 | 12.5-6.25 | |

TABLE 2-continued
Activity of test compounds (MICs in µg/mL)
| Compound | PA | SA | SC | EC | BA | EF | Mammalian Cytotoxicity* IC50 (µg/mL) |
|---|---|---|---|---|---|---|---|
| PP5138 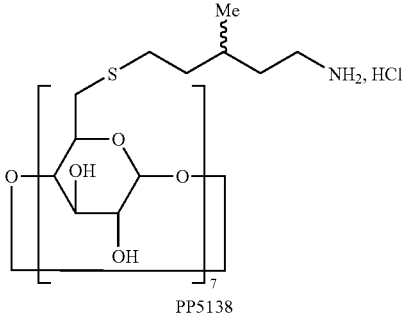 | >100 | >100 | >100 | >100 | 100-50 | >100 | |
| PP5139 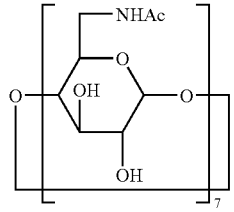 | >200 | >200 | >200 | >200 | >200 | >200 | |
| PP5140 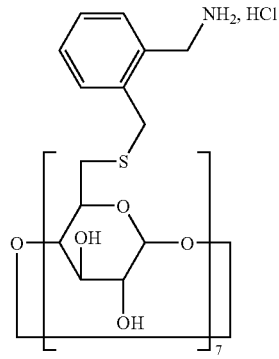 | >100 | 25-12.5 | 50-25 | 50-25 | 3.12-1.56 | >100 | 193.5 |
| PP5145 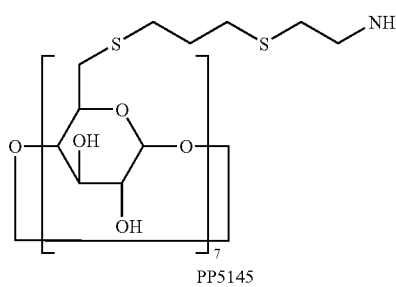 | >200 | >200 | >200 | 100-50 | 12.5-6.25 | >200 | |
*Lung cancer cells A549;
PA = *Pseudomonas aeruginosa*;
SA = *Staphylococcus aureus*;
SC = *Salmonella enterica*;
EC = *Escherichia coli*;
BA = *Bacillus atropheus*; and
EF = *Enterococcus faecalis*.

EXAMPLE 3

Potentiation of Clinically Used Antibiotics by Compounds vs. Clinical Isolates of Pseudomonas aeruginosa Numerous pathogenic bacteria have developed a resistance to many clinically used antibiotics. Following the protocols described herein, various compounds were mixed with clinically used antibiotics to treat *Pseudomonas aeruginosa* (*P. aeruginosa*). The results are shown in Tables 3 and 4 below. These results demonstrate that compounds of the invention are able to potentiate the activity of known antibiotics.

TABLE 3

Activity of known antibiotics alone or in combination with compounds of the invention

| Test Compounds | *P. aeruginosa* (susceptible clinical isolate) |
|---|---|
| Methicillin | >100 |
| Methicillin + PP5027 | 25-12.5 |
| Methicillin + PP5114 | 25-12.5 |
| Methicillin + PP5135 | 6.25-3.12 |
| Methicillin + PP5140 | 100-50 |
| Penicillin V | >100 |
| Penicillin V + PP5027 | 50-25 |
| Penicillin V + PP5114 | 50-25 |
| Penicillin V + PP5135 | 25-12.5 |
| Penicillin V + PP5140 | 50-25 |
| Vancomycin | >100 |
| Vancomycin + PP5027 | 12.5-6.25 |
| Vancomycin + PP5114 | 25-12.5 |
| Vancomycin + PP5135 | 3.12-1.56 |
| Vancomycin + PP5140 | 100-50 |

TABLE 4

Activity of known antibiotics alone or in combination with compounds of the invention (AG = Aminoglycoside)

| MIC µg/mL | Susceptible | AG Resistant | Multi-drug Resistant |
|---|---|---|---|
| Chloramphenicol | 50-25 | 50-25 | 100-50 |
| Chloramphenicol + PP5027 | 01.56-0.78 | 0.2-0.1 | 100-50 |
| Chloramphenicol + PP5113 | 3.12-1.56 | 12.5-6.25 | 12.5-6.25 |
| Chloramphenicol + PP5114 | 6.25-3.12 | 6.25-3.12 | 12.5-6.25 |
| Chloramphenicol + PP5115 | 50-25 | 3.12-1.56 | 12.5-6.25 |
| Chloramphenicol + PP5121 | 50-25 | 50-25 | 100-50 |
| Norfloxacin | 6.25-3.12 | 1.56-0.78 | >100 |
| Norfloxacin + PP5027 | 3.12-1.56 | <0.1 | >100 |
| Norfloxacin + PP5113 | 0.78-0.39 | 0.78-0.39 | >100 |
| Norfloxacin + PP5114 | 0.78-0.39 | 0.2-0.1 | >100 |
| Norfloxacin + PP5115 | 6.25-3.12 | 3.12-1.56 | >100 |
| Norfloxacin + PP5121 | 6.25-3.12 | 1.56-0.78 | >100 |
| Tobramycin | 0.39-0.2 | 12.5-6.25 | >100 |
| Tobramycin + PP5027 | 0.78-0.39 | 0.2-0.1 | >100 |
| Tobramycin + PP5113 | <0.1 | 25-12.5 | 100-50 |
| Tobramycin + PP5114 | <0.1 | 3.12-1.56 | >100 |
| Tobramycin + PP5115 | <0.1 | 3.12-1.56 | >100 |
| Tobramycin + PP5121 | 0.39-0.2 | 12.5-6.25 | >100 |

EXAMPLE 4

Compounds Retain Activity Against Methicillin Resistant

Methicillin-resistant *staphylococcus aureus* is a bacterial infection resistant to antibiotic methicillin and can no longer be killed by this antiobiotic. Following the protocols described herein, various compounds were used antibiotics to treat *Staphylococcus aureus* (Methicillin resistant). The results are shown in Table 5 below. These results below demonstrate that compounds of the invention are able to retain activity against Methicillin resistance.

TABLE 5

Activity of compounds against Methicillin Resistance

| *Staphylococcus aureus*\* (susceptible) | | *Staphylococcus aureus* (Methicillin resistant) | |
|---|---|---|---|
| Compound | MIC µg/mL | Compound | MIC µg/mL |
| PP5073 | 3.12-1.56 | PP5073 | 3.12-1.56 |
| PP5094 | 3.12-1.56 | PP5094 | 3.12-1.56 |
| PP5098 | 3.12-1.56 | PP5098 | 6.25-3.12 |
| PP5105 | 3.12-1.56 | PP5105 | 3.12-1.56 |
| PP5125 | 3.12-1.56 | PP5125 | 6.25-3.12 |

*ATCC 700698

What is claimed is:

1. A method for potentiating the activity of an antibiotic to inhibit the growth of a bacterium which is resistant to said antibiotic, comprising contacting the bacterium with said antibiotic and a compound having the formula

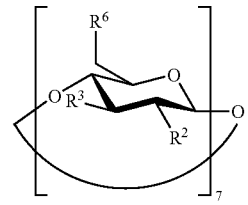

wherein $R_2$ is H, OH, OAc, or $O(CH_2CH_2O)_n$; $R_3$ is H, OH, OAc, $OSO_3Na$, or $NH_2$; and $R_6$ is H, $NH_2$, $S(CH_2)_mNH_2$, I, $N_3$, SH, lower alkyl, S-alkylguanidyl, O-alkylguanidyl, S-aminoalkyl, O-aminoalkyl, aminoalkyl, aralkyl, aryl, heterocyclic ring(s), $OSO_3Na$ or N which is mono, di or trisubstituted with alkyl, aralkyl, aryl, heterocyclic ring or heterocyclic alkyl, and any of which substituents can be further substituted with N, O or S which can be further substituted with H, alkyl, aralkyl or aryl, wherein n is from about 1 to about 10, and wherein m is from about 1 about 10.

2. The method according to claim 1, wherein for each of $R_2$, $R_3$ and $R_6$ any one or more of the carbon atoms may be optionally replaced by S, N or O.

3. The method according to claim 1, wherein the bacterium is in a mammal.

4. The method according to claim 3, wherein the mammal is a human.

5. The method according to claim 1, wherein the compound has the formula

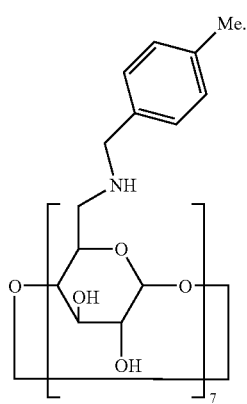
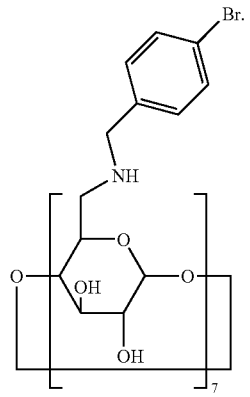
6. The method according to claim 1, wherein the compound is
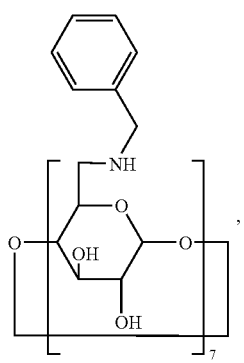
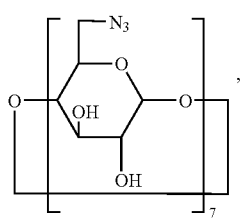
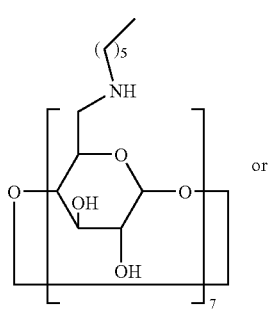
or
7. The method according to claim 1, wherein the compound is
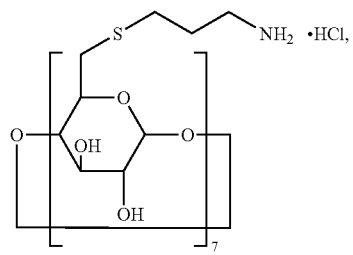
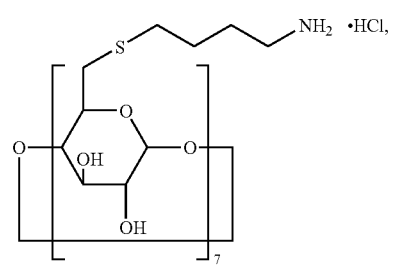
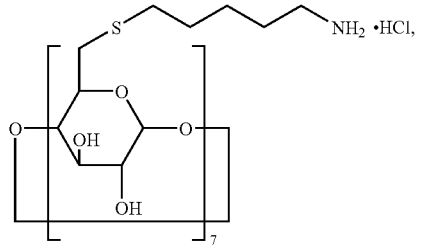
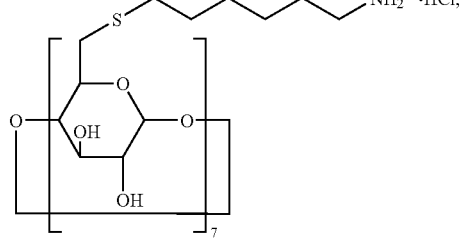

87
-continued
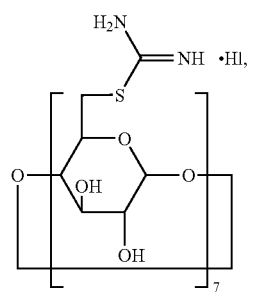
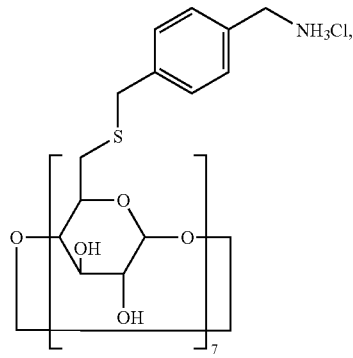
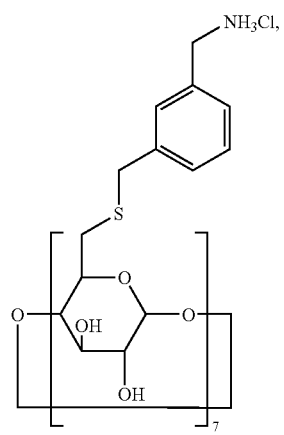
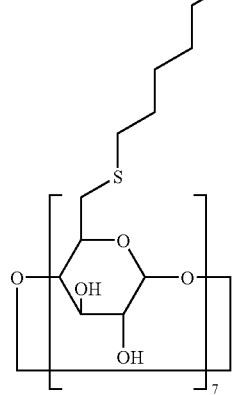
88
-continued
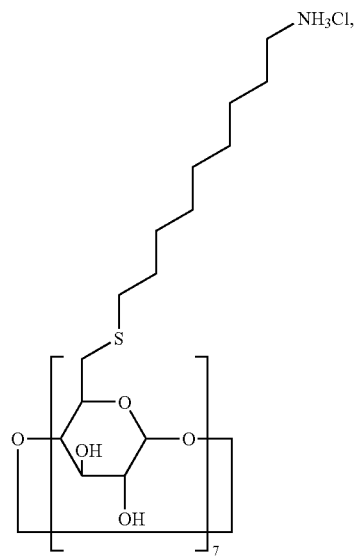
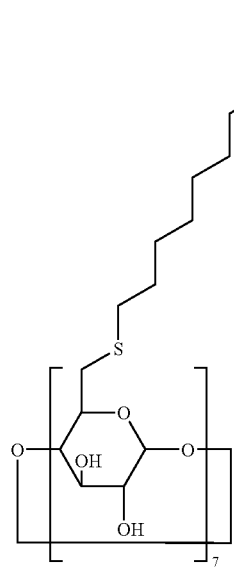
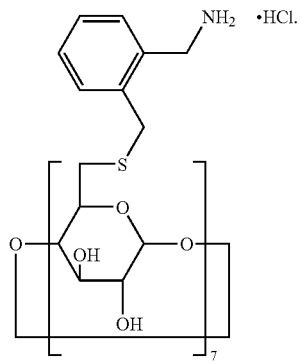

8. The method according to claim 1, wherein the compound is
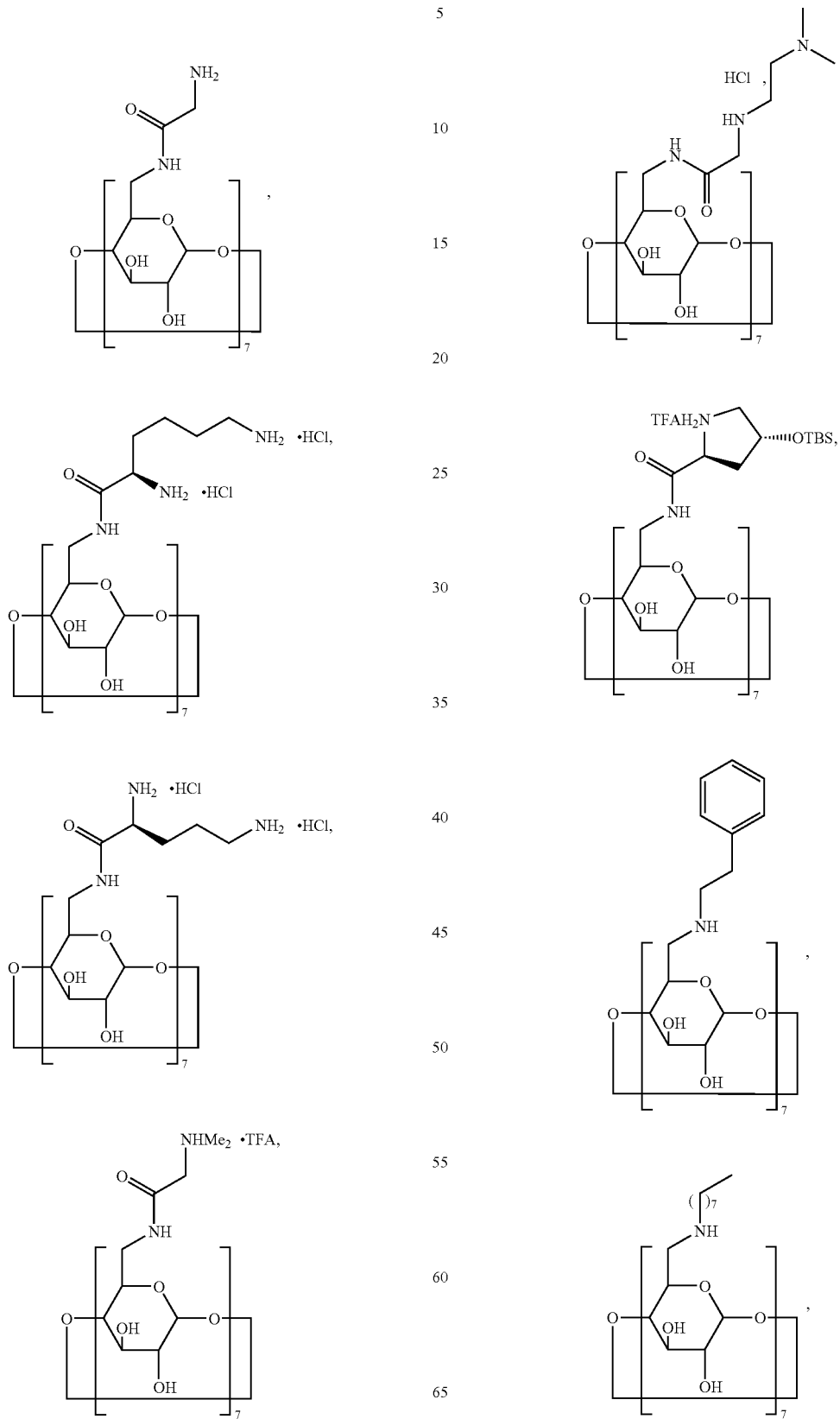

91
-continued
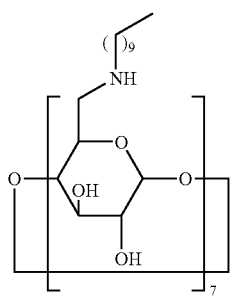
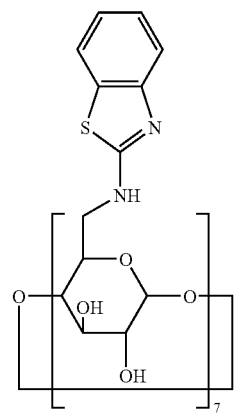
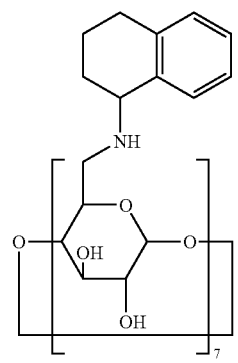
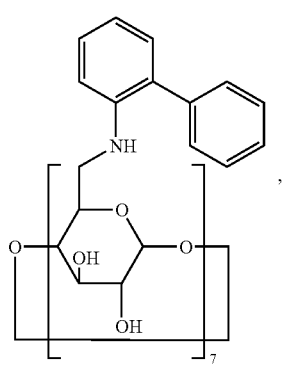
92
-continued
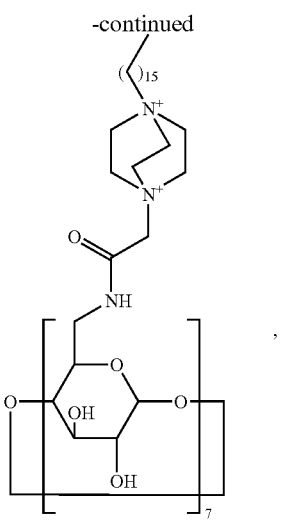
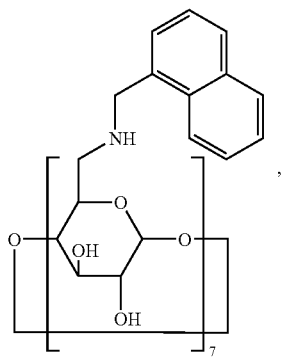
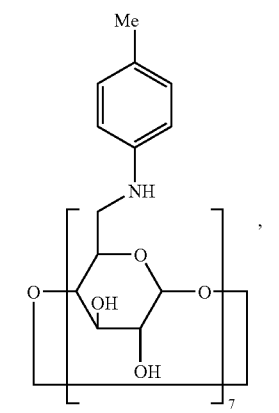
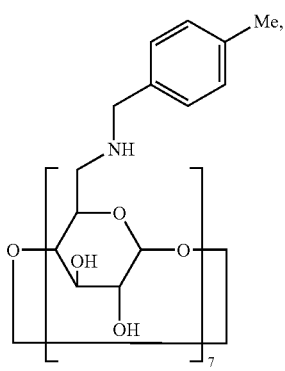

-continued

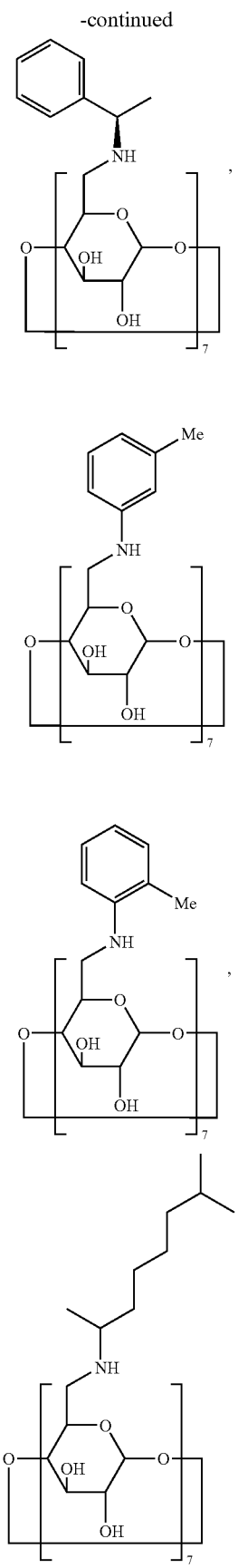

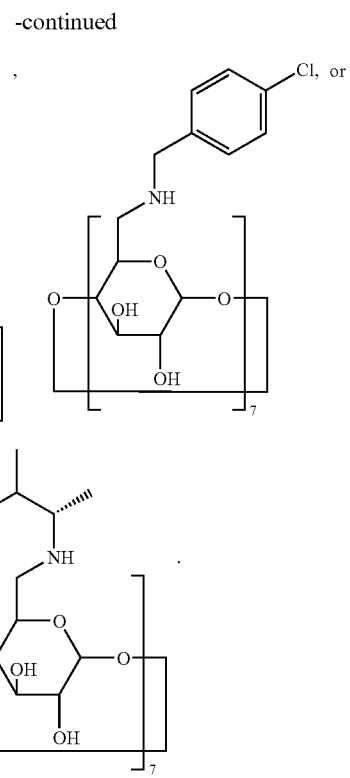

9. The method according to claim 1, wherein the antibiotic is Methicillin, Penicillin, Vancomycin, Chloramphenicol, Norfloxacin or Tobramycin.

10. The method according to claim 9, wherein the antibiotic is Methicillin.

11. The method according to claim 9, wherein the antibiotic is Penicillin.

12. The method according to claim 9, wherein the antibiotic is Vancomycin.

13. The method according to claim 9, wherein the antibiotic is Chloramphenicol.

14. The method according to claim 9, wherein the antibiotic is Norfloxacin.

15. The method according to claim 9, wherein the antibiotic is Tobramycin.

16. The method according to claim 5, wherein the antibiotic is Methicillin, Penicillin, Vancomycin, Chloramphenicol, Norfloxacin or Tobramycin.

17. The method according to claim 16, wherein the antibiotic is Methicillin.

18. The method according to claim 16, wherein the antibiotic is Penicillin.

19. The method according to claim 16, wherein the antibiotic is Vancomycin.

20. The method according to claim 16, wherein the antibiotic is Chloramphenicol.

21. The method according to claim 16, wherein the antibiotic is Norfloxacin.

22. The method according to claim 16, wherein the antibiotic is Tobramycin.

23. The method according to claim 6, wherein the antibiotic is Methicillin, Penicillin, Vancomycin, Chloramphenicol, Norfloxacin or Tobramycin.

24. The method according to claim 23, wherein the antibiotic is Methicillin.

25. The method according to claim 23, wherein the antibiotic is Penicillin.

26. The method according to claim 23, wherein the antibiotic is Vancomycin.

27. The method according to claim 23, wherein the antibiotic is Chloramphenicol.

28. The method according to claim 23, wherein the antibiotic is Norfloxacin.

29. The method according to claim 23, wherein the antibiotic is Tobramycin.

30. The method according to claim 7, wherein the antibiotic is Methicillin, Penicillin, Vancomycin, Chloramphenicol, Norfloxacin or Tobramycin.

31. The method according to claim 30, wherein the antibiotic is Methicillin.

32. The method according to claim 30, wherein the antibiotic is Penicillin.

33. The method according to claim 30, wherein the antibiotic is Vancomycin.

34. The method according to claim 30, wherein the antibiotic is Chloramphenicol.

35. The method according to claim 30, wherein the antibiotic is Norfloxacin.

36. The method according to claim 30, wherein the antibiotic is Tobramycin.

37. The method according to claim 8, wherein the antibiotic is Methicillin, Penicillin, Vancomycin, Chloramphenicol, Norfloxacin or Tobramycin.

38. The method according to claim 37, wherein the antibiotic is Methicillin.

39. The method according to claim 37, wherein the antibiotic is Penicillin.

40. The method according to claim 37, wherein the antibiotic is Vancomycin.

41. The method according to claim 37, wherein the antibiotic is Chloramphenicol.

42. The method according to claim 37, wherein the antibiotic is Norfloxacin.

43. The method according to claim 37, wherein the antibiotic is Tobramycin.

44. The method according to claim 1, wherein $R^2$ and $R^3$ are OH.

* * * * *